US006846957B2

(12) United States Patent
Zelenin

(10) Patent No.: US 6,846,957 B2
(45) Date of Patent: Jan. 25, 2005

(54) SYNTHESIS OF 3-AMINOMETHYL-1-PROPANOL, A FLUOXETINE PRECURSOR

(75) Inventor: Alexander Zelenin, San Antonio, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 17 days.

(21) Appl. No.: 10/302,806

(22) Filed: Nov. 22, 2002

(65) Prior Publication Data

US 2004/0102651 A1 May 27, 2004

(51) Int. Cl.[7] ..................... C07C 223/00; A61K 31/135
(52) U.S. Cl. ....................... 564/343; 564/347; 564/342; 514/649; 514/651
(58) Field of Search .................. 564/342, 343, 564/347; 514/649, 651

(56) References Cited

U.S. PATENT DOCUMENTS

| | | | |
|---|---|---|---|
| 4,194,009 A | 3/1980 | Molloy et al. | 424/330 |
| 4,296,126 A | 10/1981 | Nedelec et al. | 424/316 |
| 4,314,081 A | 2/1982 | Molloy et al. | 564/347 |
| 4,902,710 A | 2/1990 | Foster et al. | 514/438 |
| 5,104,899 A | 4/1992 | Young et al. | 514/646 |
| 5,166,437 A | 11/1992 | Kairisalo et al. | 564/347 |
| 5,225,585 A | 7/1993 | Schwartz et al. | 558/275 |
| 5,310,756 A | 5/1994 | Jakobsen et al. | 514/524 |
| 5,356,934 A | 10/1994 | Robertson et al. | 514/649 |
| 5,708,035 A | 1/1998 | Young et al. | 514/649 |
| 5,760,243 A | 6/1998 | Theriot | 548/240 |
| 5,936,124 A | 8/1999 | Hilborn et al. | 564/347 |
| 6,025,517 A | 2/2000 | Hilborn et al. | 560/27 |

FOREIGN PATENT DOCUMENTS

| | | |
|---|---|---|
| EP | 0380924 | 8/1990 |
| EP | 0457559 | 11/1991 |
| EP | 0529842 | 3/1993 |
| ES | 2101650 | 7/1997 |
| ES | 2103681 | 9/1997 |
| FI | 81083 | 5/1990 |
| GB | 2060618 | 5/1981 |
| HU | 207035 | 3/1993 |
| WO | WO 93/09769 | 5/1993 |
| WO | WO 94/00416 | 1/1994 |
| WO | WO 98/11054 | 3/1998 |
| WO | WO 99/05129 | 2/1999 |
| WO | WO 99/06362 | 2/1999 |
| WO | WO 99/67196 | 12/1999 |
| WO | WO 00/07976 | 2/2000 |
| WO | WO 00/21917 | 4/2000 |
| WO | WO 00/37425 | 6/2000 |
| WO | WO 01/44166 | 6/2001 |

OTHER PUBLICATIONS

CAS Online Printout 1955:16022;, Hirao, RN=877–50–9.*
Ager and Laneman, "Reductions of 1,3–dicarbonyl systems with ruthenium–biary1bisphosphine catalysts," *Tet. Asymmetry*, 8(20)3327–3355, Report No. 30, 1997.
Arce, "Process for the preparation of fluoxetine and its addition salts," *Chem. Abstr.*, 129:260223, 1998.
Bartoli et al., "Convenient procedure for the reduction of β–enamino ketones: synthesis of γ–amino alcohols and tetrahydro–1,3–oxazines," *J. Chem. Soc.*, 1:537–543, 1994.
Chatterjee and Rudorf, "Reaction of enaminones with thiacumulenes," In: *Phosphorus, Sulfur and Silicon and the Related Elements*, 133:251–266, 1998.
Chenevert and Fortier, "Chemoenzymatic synthesis of both enantiomers of fluoxetine," *Chem. Lett.*, 9:1603–1606, 1991.
Corey and Reichard, "Enantioselective and practical synthesis of R– and S–fluoxetines," *Tetrahedron Lett.*, 30(39):52075210, 1989.
Gao and Sharpless, "Asymmetric synthesis of both enantiomers of tomoxetine and fluoxetine. Selective reduction of 2,3–epoxycinnamyl alcohol with red–A1," *J. Org. Chem.*, 53:4081–4084, 1988.
Hilborn et al., "Fluoxetine chiral process from benzoylpropionic acid," *Chem. Abstr.*, 131:170168, 1999.
Kairisalo et al.., "New method for preparation of fluoxetine hydro–chloride," *Chem. Abstr.*, 114:42266,1991.
Kumar and Dike, "A novel chemoenzymatic enantioselective synthesis of some clinically effective CNS drugs and related compounds," *Indian J. Chem.*, 31B:803–809, 1992.
Kumar et al., "A new chemoenzymatic enantioselective synthesis of R–(–)–tomoxetine, (R)– and (S)–fluoxetine," *Tetrahedron Lett.*, 32:1901–1904, 1991.
Mitchell and Koenig,"Synthesis of R– and S–fluoxetine norfluoxetine and related compounds from styrene oxide," *Synth. Commun.*, 25:1231–1238, 1995.
Pedregal, "Preparation of fluoxetine via the Michael addition," *Chem. Abstr.*, 128:114779, 1998.
Robertson et al. "Synthesis of 14C– and 3H–labeled fluoxetine, a selective serotonin uptake inhibitor," *J. Labeled Compound Radiopharm.*, 24:1397–1404, 1987.
Robertson et al., "Absolute configurations and pharmacological activities of the optical isomers of fluoxetine, a selective serotonin–uptake inhibitor," *J. Med. Chem.*, 31:1412–1417, 1988.

(List continued on next page.)

*Primary Examiner*—Samuel Barts
(74) *Attorney, Agent, or Firm*—Fulbright & Jaworski L.L.P.

(57) ABSTRACT

The present invention concerns a method of synthesizing fluoxetine hydrochloride. The method includes the synthesis of 3-methylamino-1-phenyl-1-propanol by reduction of 1-phenyl-3-methylamino-2-propen-1-one with sodium borohydride and acetic acid.

13 Claims, No Drawings

OTHER PUBLICATIONS

Sakuraba and Achiwa, "Efficient asymmetric hydrogenation of β– and γ–amino ketone derivatives leading to practical synthesis of fluoxetine and eprozinol," *Chem. Pharm. Bull.*, 43:748–753, 1995.

Sakuraba and Achiwa,"Practical asymmetric synthesis of (R)–fluoxetine hydrochloride catalyzed by (2S, 4S)–4–dicyclohexylphosphino–2–diphenylphosphinomethy l–1–(N–methylcarbamoyl)pyrrolidine–rhodium comples," *Syn. Lett.*, 689–690, 1991.

Schwartz et al., "Preparation of fluoxetine," *Chem. Abstr.*, 119:8485, 1993.

Theriot, "Preparation and use of 2–methyl–5–phenylisoxazolidine," *Chem. Abstr.*, 129:54356, 1998.

Theriot, "Preparation of hydrocarbyInitrones as isoxazolidine precursors," *Chem. Abstr.* 130:153652, 1999.

Weber and Marti, "Amination and etherification method for producing fluoxetine," *Chem. Abstr.*, 133: 58607, 2000.

Wirth et al., "Identification and comparison of impurities in fluoxetine hydrochloride synthesized by seven different routes," *Organic Proc. Res. Dev.*, 4:513–519, 2000.

Young and Barberich, "Methods and compositions for treating depression using optically pure fluoxetine," *Chem. Abstr.*, 117:7635, 1992.

Young and Barberich, "Preparation of and pharmaceutical formulations utilizing pure (S+) enantomer fluoxetine," *Chem. Abstr.*, 119:203106, 1993.

* cited by examiner

SYNTHESIS OF 3-AMINOMETHYL-1-PROPANOL, A FLUOXETINE PRECURSOR

BACKGROUND OF THE INVENTION

1. Field of the Invention

The present invention relates generally to the fields of chemical synthesis. More particularly, it concerns the synthesis of 3-aminomethyl-1-propanol, a Fluoxetine precursor.

2. Description of Related Art

Fluoxetine is a selective serotonin uptake inhibitor presently available for the treatment of depression under the trade name Prozac™. Its chemical name is typically N-methyl-3-phenyl-3-[(α,α,α-trifluoro-p-tolyl)oxy]propyl amine in much of the literature; its name for indexing in Chemical Abstracts is (±)-N-methyl-γ-[4-(trifluoromethyl) phenoxy] benzenepropanamine. Thus, improved processes for the commercial preparation of fluoxetine are of considerable value.

Numerous processes are known in the literature. The original U.S. Patents to fluoxetine (U.S. Pat. Nos. 4,314,081 and 4,194,009) describe syntheses beginning from 3-dimethylaminopropiophenone, which is reduced with diborane, chlorinated with thionyl chloride, condensed with 4-trifluoromethylphenol, and demethylated with cyanogen bromide and potassium hydroxide in ethylene glycol. This process was somewhat improved by Robertson et al. (1987) by condensing the alcohol with 4-chlorobenzotrifluoride and by replacing cyanogen bromide with phenylchloroformate.

European application 529842 discloses an improved process in which 3-dimethylamino-1-phenyl-1-propanol is reacted with an alkyl chloroformate and hydrolyzed to provide 3-methylamino-1-phenyl-1-propanol, which is then condensed with 4-chloro- or 4-fluorobenzotrifluoride. European application 457559 describes a chiral synthesis of the 3-dimethylamino-1-phenyl-1-propanol that is used as a starting material in the foregoing European application. The chiral synthesis is accomplished by reduction of the corresponding ketone with lithium aluminum hydride using (2R, 3S)-(−)4-dimethylamino-1,2,-diphenyl-3-methyl-2-butanol as a chiral ligand. A similar chiral reduction has been described by Sakuraba et al. (1991) using a different chiral reducing agent. Another approach, described in European patent 380924, proceeds by reduction of ethylbenzoylacetate and subsequent aminolysis of the ethyl ester with methylamine. The reduction of ethylbenzoylacetate can also be accomplished in an enantioselective manner using baker's yeast (Kumar et al., 1992). A ruthenium catalyst having a chiral ligand has been employed in a similar catalytic reduction by Ager and Laneman, (1997).

One of the key intermediates of fluoxetine synthesis is 3-(methylamino)-1-phenyl-1-propanol (Formula 1). There are three general approaches to the synthesis of this aminoalcohol. The first method is based on the reduction of the carbonyl group of 3-substituted propiophenones (halo, dialkylamino, amido, carboethoxy) followed by the conversion of the above functionalities into the methylamino group (U.S. Pat. Nos. 4,902,710 and 5,936,124; Finnish Patent FI 81083; European Application EP 529842; Spanish Patents, ES 2101650 and ES 2103681; International Application WO 0037425; Foster et al., 1990; Kairisalo et al., 1990; Schwartz et al., 1993; Pedregal, 1997; Arce, 1997; Weber and Marti, 2000; Robertson et al., 1988; Corey and Reichard, 1989; Kumar et al., 1991; Chenevert, 1991; Sakuraba, 1995; and Hilborn et al., 1999). In the second approach, phenylisoxazolidine is synthesized first, and then transformed into 3-(methylamino)-1-phenyl-1-propanol by reductive ring cleavage (U.S. Pat. No. 5,760,243; Int. Appl. WO 9906362; Theriot, 1998; Theriot, 1999; and Wirth et al., 2000). The third general method is based on the ring opening of epoxystyrene or its derivatives followed by the conversion of 3-functionally substituted 1-phenylpropanols into 3-(methylamino)-1-phenyl-1-propanol (U.S. Pat. No. 5,104, 899; PCT Int. Appl. WO 9309769; Gao and Sharpless, 1988; Young and Barberich, 1993; Young and Barberich, 1992; and Mitchell and Koenig, 1995). Although the majority of the reported syntheses of 3-(methylamino)-1-phenyl-1-propanol are simple and efficient, some of them require two reduction steps, which lowers overall yields.

SUMMARY OF THE INVENTION

The present invention provides a novel method of synthesizing a 3-methylamino-1-phenyl-1-propanol precursor that may be used in the preparation of fluoxetine (Prozac™). In various embodiments, the invention includes methods for preparing fluoxetine that includes a) synthesizing 1-phenyl-1-3-methylamino-2-propen-1-one by i) claisen condensation of acetophenone with ethyl formate leading to benzoylacetaldehyde sodium salt and ii) condensation of the benzoylacetaldehyde sodium salt with methylamine hydrochloride; b) converting 1phenyl-3-methylamino-2-propen-1-one into 3-methylamino-1-phenyl-1-propanol using sodium borohydride and acetic acid; and c) converting 3-methylamino-1-phenyl-1-propanol to Fluoxetine hydrochloride. Converting 1-phenyl-3-methylamino-2-propen-1-one into 3-methylamino-1-phenyl-1-propanol using a sodium borohydride and acetic acid may include, for example adding approximately 21 mmol of sodium borohydride to a solution comprising approximately 3.7 mmol of 3-methylamino-1-phenyl-2-propen-1-one in a glacial acetic acid solution producing a 3-methylamino-1-phenyl-1-propanol solution. The adding of sodium borohydride may be performed at about 1, 2, 3, 4, 5 to 10, 11, 12, 13, 14, 15° C. or higher. The inventive methods may further comprise adding approximately 240 mmol sodium hydroxide to the 3-methylamino-1-phenyl-1-propanol solution. In certain embodiments, the methods described herein may include extracting the 3-methylamino-1-phenyl-1-propanol solution with ethyl acetate. Furthermore, the methods may include evaporating the solvent of the 3-methylamino-1-phenyl-1-propanol solution.

In various embodiments, converting 3-methylamino-1-phenyl-1-propanol to Fluoxetine hydrochloride may comprise a) reacting 3-methylamino-1-phenyl-1-propanol with 4-chlorobenzotrifluoride in the presence of sodium borohydride in dimethylsulfoxide to give fluoxetine free base; and b) preparing fluoxetine hydrochloride by reacting the fluoxetine free base with hydrochloric acid in ether.

In certain embodiments of the invention the methods may include preparing 3-methylamino-1-phenyl-1-propanol comprising the steps of: a) Claisen condensation of acetophenone with ethyl formate leading to benzoylacetaldehyde sodium salt; b) condensation of the benzoylacetaldehyde sodium salt with a methylamine hydrochloride; and c) converting 1-phenyl-3-methylamino-2-propen-1-one into 3-methylamino-1-phenyl-1-propanol by reacting 1-phenyl-3-methylamino-2-propen-1-one with sodium borohydride and acetic acid. The condensation of the crude benzoylacetaldehyde sodium salt with methylamine hydrochloride may include the steps of adding approximately 29.4 mmol of benzoylacetaldehyde sodium salt to an solution containing approximately 148 mmol of methyl amine hydrochloride to produce a 3-methylamino-1-phenyl-1-propanol precipitate.

The methods may further include filtering; washing with water or other appropriate compound, liquid or solution; and drying the 3-methylamino-1-phenyl-1-propanol precipitate. Converting 1-phenyl-3-methylamino-2-propen-1-one into 3-methylamino-1-phenyl-1-propanol may include adding approximately 21 mmol of sodium borohydride to a solution comprising approximately 3.7 mmol of 3-methylamino-1-phenyl-2-propen-1-one in a glacial acetic acid solution producing a 3-methylamino-1-phenyl-1-propanol solution.

In some embodiments, fluoxetine hydrochloride may be prepared by methods including the steps of: a) synthesizing 1-phenyl-3-methylamino-2-propen-1-one by i) claisen condensation of acetophenone with ethyl formate leading to benzoylacetaldehyde sodium salt and ii) condensation of the benzoylacetaldehyde sodium salt with methylamine hydrochloride producing 1-phenyl-3-methylamino-1-propenone; b) converting 1-phenyl-3-methylamino-2-propen-1-one into 3-methylamino-1-phenyl-1-propanol by using sodium borohydride and acetic acid; and c) converting 3-methylamino-1-phenylpropanol to Fluoxetine hydrochloride.

In certain embodiments, a 3-methylamino-1-phenyl-1-propanol compound prepared by the method comprising: a) claisen condensation of acetophenone with ethyl formate leading to benzoylacetaldehyde sodium salt; b) condensation of the crude benzoylacetaldehyde sodium salt with an methylamine hydrochloride producing 1-phenyl-3-methylamino-2-propen-1-one; and c) converting 1-phenyl-3-methylamino-2-propen-1-one into 3-methylamino-1-phenyl-1-propanol by reacting 1-phenyl-3-methylamino-2-propen-1-one with sodium borohydride and acetic acid. Converting 1-phenyl-3-methylamino-2-propen-1-one into 3-methylamino-1-phenyl-1-propanol using sodium borohydride and acetic acid may comprise adding approximately 21 mmol of sodium borohydride to a solution comprising approximately 3.7 mmol of 3-methylamino-1-phenyl-2-propen-1-one in a glacial acetic acid solution producing a 3-methylamino-1-phenyl-1-propanol solution. The adding of sodium borohydride may be performed at about 1, 2, 3, 4, 5 to 10, 11, 12, 13, 14, 15° C. or more. The methods may further comprise adding approximately 240 mmol sodium hydroxide to the 3-methylamino-1-phenyl-1-propanol solution. The 3-methylamino-1-phenyl-1-propanol solution may be extracted with an ethyl acetate solution or another appropriate liquid or solution. The method may further comprise evaporating the solvent of the 3-methylamino-1-phenyl-1-propanol solution.

Certain embodiments of the invention include a pharmaceutical composition comprising fluoxetine hydrochloride prepared by methods comprising: a) synthesizing 1-phenyl-3-methylamino-2-propen-1-one by i) claisen condensation of acetophenone with ethyl formate leading to bezoylacetaldehyde sodium salt and ii) condensation of the benzoylacetaldehyde sodium salt with methylamine hydrochloride producing 1-phenyl-3-methylamino-2-propen-1-one; b) converting 1-phenyl-3-methylamino-2-propen-1-one into 3-methylamino-1-phenyl-1-propanol by using sodium borohydride and acetic acid; and c) converting 3-methylamino-1-phenyl-1-propanol to Fluoxetine hydrochloride.

The use of the word "a" or "an" when used in conjunction with the term "comprising" in the claims and/or the specification may mean "one," but it is also consistent with the meaning of "one or more," "at least one," and "one or more than one."

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF ILLUSTRATIVE EMBODIMENTS

A new efficient synthetic method for a racemic mixture of 3-(methylamino)-1-phenyl-1-propanol (Formula 1), a key intermediate in various schemes for the synthesis of fluoxetine (Prozac™; Formula 2), is described herein. The method is based on the reduction of 3-(methylamino)-1-phenyl-2-propen-1-one (1-phenyl-3-methylamino-1-propenone (Formula 3)), with a reducing agent in an acid solution. Certain embodiments of the invention include reduction of 3-(methylamino)-1-phenyl-2-propen-1-one (1-phenyl-3-methylamino-1-propenone (Formula 3)), with sodium borohydride in acetic acid.

The overall synthesis described in Scheme 1 can be further characterized as a process that begins with the preparation of 3-(methylamino)-1-phenyl-2-propen-1-one by a Claisen condensation of acetophenone and ethyl formate (see Clesse and Quinon, 1969 for a general description of Claisen condensation). 3-(methylamino)-1-phenyl-2-propen-1-one (Formula 3) is subsequently converted into 3-(methylamino)-1-phenyl-1-propanol (Formula 1) by using sodium borohydride and acetic acid. Synthesis of fluoxetine from 3-(methylamino)-1-phenyl-1-propanol (Formula 1) may then be accomplished by various synthetic methods, see below for examples.

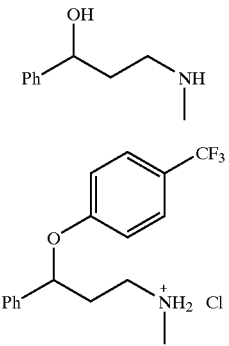

Formula 1

Formula 2

In certain embodiments, the synthetic approach is hydride reduction of 3-(methylamino)-1-phenyl-2-propen-1-one (Formula 3). This functionalized propriophenone may be prepared using Claisen condensation of acetophenone with ethyl formate leading to benzoylacetaldehyde sodium salt as an intermediate followed by the condensation of the crude salt with methylamine hydrochloride. The reduction reaction of propiophenone derivative is carried out in acetic acid using sodium borohydride as a reducing agent, it is contemplated that other reducing agents may also be used. Both carbonyl and azomethyne functions undergo reduction under these conditions leading to the target aminoalcohol with a high yield. The use of an acid, in particular acetic acid in the reduction step is crucial. Attempts to apply the conventional sodium borohydride/tetrahydrofuran mixture have failed. The described three-step sequence does not require, but may include chromatography, distillation or other purification operations and involves readily available non-hazardous inexpensive materials. One advantage of 3-(Methylamino)-1-phenyl-2-propen-1-one is that it may be directly reduced to the target aminoalcohol. Another advantage is the synthetic simplicity of the reaction methods.

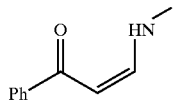

Formula 3

Certain embodiments of the invention include the simultaneous reduction of both carbonyl and azomethyne functions of 3-(methylamino)-1-phenyl-2-propen-1-one (Formula 3). Attempts to apply conventional sodium borohydride/methanol or lithium aluminum hydride/tetrahydrofuran mixtures under various conditions failed. Also, using the same starting material under more forcing conditions various unidentified products were produced. These results may be explained by a low reactivity of enaminoketones and enaminoaldehydes toward hydride reduction, which is due to a fully conjugated stable enaminone unit (Bartoli et al., 1994). One of the various breakthrough of the inventive methods occurred when acetic acid was used instead of methanol in a combination with sodium borohydride under mild conditions.

In brief, exemplary methods include sodium borohydride (800 mg, 21.0 mmol) added in portions to a vigorously stirred solution of 3-methylamino-1-phenyl-2-propen-1-one (600 mg, 3.7 mmol) in glacial acetic acid (15 ml) over a period of 30 minutes at 5 to 10° C. The reaction mixture was stirred for another 30 minutes at the same temperature, and then for 3 hours at room temperature. Work up was done using 4 M aqueous sodium hydroxide (60 ml) that was added dropwise under cooling (water/ice bath). The resulting mixture was extracted with ethyl acetate (3 times 70 ml), washed with water (50 ml), and dried (Na$_2$SO$_4$). Evaporation of the solvent under reduced pressure gave 470 mg (77%) of 3-methylamino-1-phenyl-1-propanol as yellow oil.

A similar transformation was also achieved by the use of a mixture of sodium metal (6 equiv.), isopropanol and tetrahydrofuran (Table 1, entry 2) under the conditions of the electron transfer reduction reported recently for a similar reaction of a series of enaminones (see Bartoli et al, 1994 for exemplary methods). Unfortunately, the yield was only 55%; and the reduction product contained impurities that were difficult to remove.

Scheme 1

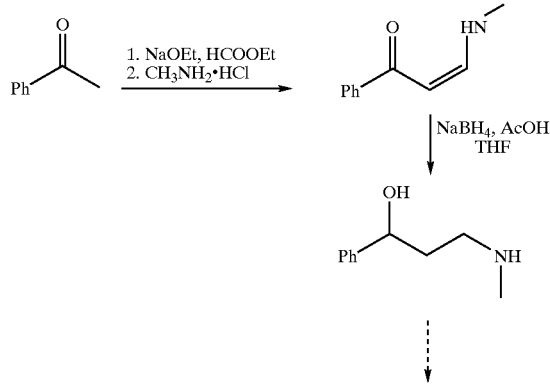

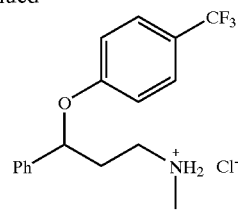

Synthesis of Fluoxetine

Once 3-(methylamino)-1-phenyl-2-propen-1-one (Formula 3) is synthesized by the inventive methods the conversion of 3-(methylamino)-1-phenyl-1-propanol (Formula 1) may be accomplished by a variety of known methods. The methods include, but are not limited to the following examples.

One process for the preparation of fluoxetine is described in GB Patent No. 2,060,618 (incorporated herein by reference) which comprises reacting sodium salt of N-methyl-3-hydroxy-3-phenylpropylamine (formed with sodium hydride in dimethyl sulphoxide) with 1-fluoro-4-(trifluoromethyl)benzene at high temperature.

Another process described in Hungarian Patent No. 207,035 (incorporated herein by reference), fluoxetine is prepared by the etherification of N-methyl-3-hydroxy-3-phenyl propylamine with 1-chloro-4-trifluoromethyl benzene in the presence of sodium amide as a base using dimethylsulfoxide as a solvent.

In other examples, such as U.S. Pat. No. 5,166,437 (incorporated herein by reference), the above etherification step which is carried out in solvents such as N-methyl pyrrolidone or dimethyl sulphoxide in the presence of potassium t-butoxide.

U.S. Pat. No. 5,225,585 (incorporated herein by reference) describes a process which involves use of sodium hydride in dimethylacetamide/toluene mixture for the etherification step.

The process according to international application WO 94/00416 (incorporated herein by reference) involves the etherification of N-methyl-3-hydroxy-3-phenyl propylamine with 1-chloro-4-trifluorormethyl benzene in the presence of potassium hydroxide or sodium hydroxide in DMSO at a temperature between 50–120° C. for 4 to 20 hours.

According to international application WO 01/44166 (incorporated herein by reference) there is provided a process for the preparation of fluoxetine and its pharmaceutically acceptable salt, preferably hydrochloride. The process comprises reacting N-methyl-3-hydroxy-3-phenyl propylamine with 1-chloro-4-(trifluoromethyl)benzene in the presence of alkaline metal hydroxide in sulfolane in the presence of a catalyst.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1
Preparation of 3-(Methylamino)-1-phenyl-2-propen-1-one 3-(Methylamino)-1-phenyl-2-propen-1-one was synthesized in two steps with a 70% overall yield by the Claisen condensation of acetophenone with ethyl formate followed by the treatment of the intermediate benzoylacetaldehyde sodium salt with methylamine hydrochloride according to a Scheme 2 (see Chatterjee and Rudorf, 1998 for a general description of various reactions). The crude benzoylacetaldehyde sodium salt was treated with 5 M aqueous methylamine hydrochloride (5 equivalents); the yellow crystals of 3-(Methylamino)-1-phenyl-2-propen-1-one, collected after 2 days, were spectrally pure (85% yield).

Example 2
Reduction of 3-(Methylamino)-1-phenyl-2-propen-1-one with NaBH$_4$ in HOAc.

Acetic acid was used instead of methanol in combination with sodium borohydride under mild conditions for the reduction of 3-(methylamino)-1-phenyl-2-propen-1-one. Sodium borohydride (6 equivalents) was slowly added to a 0.25 M solution of 3-(methylamino)-1-phenyl-2-propen-1-one (Formula 3), in glacial acetic acid at 5–10° C. after stirring for 3 hours at room temperature followed by the usual work-up, the target aminoalcohol was isolated with a 77% yield (Table 1, entry 1). The effectiveness of this method may be due to the enhanced activity of both carbonyl and azomethyne groups under acidic conditions.

In a particular example, NaBH$_4$ (800 mg, 21.0 mmol) was added in portions to a vigorously stirred solution of 3-(methylamino)-1-phenyl-2-propen-1-one (600 mg, 3.7 mmol) in glacial HOAc (15 mL) over a period of 30 min at 5–10° C. The reaction mixture was stirred for another 30 min at the same temperature, and then for 3 hours at room temperature. Work-up was done using 4 M aqueous sodium hydroxide (60 mL) that was added dropwise under water/ice bath cooling (the pH of the resulting solution was about 12). The resulting mixture was extracted with EtOAc (3×70 mL), washed with H$_2$O (50 mL), and dried (Na$_2$SO$_4$). Evaporation of the solvent under reduced pressure gave 470 mg (77%) of 2 as yellow oil.

A similar transformation was also achieved by the use of a mixture of sodium metal (6 equiv.), isopropanol and tetrahydrofuran (Table 1, entry 2) under the conditions of the electron transfer reduction reported recently for a similar reaction of a series of enaminones. Unfortunately, the yield was only 55%; and the reduction product contained some impurities that were difficult to remove.

TABLE 1
Reduction of 3-(Methylamino)-1-phenyl-2-propen-1-one.

| Entry | Reducing agent | Isolated Yield (%) |
|---|---|---|
| 1 | NaBH4, HOAc | 77 |
| 2 | Na, i-PrOH | 55 |

The new convenient approach leading to the racemic mixture of 3-(methylamino)1-phenyl-1-propanol compliments existing methods. However, unlike some previous routes, the new method takes advantage of using one reduction step only.

Example 3
Preparation of Fluoxetine Free Base

To a 3.0 L round bottom flask is added 24.5 g (0.148 mol) of the aminoalcohol and this is dissolved in 215 mL of DMSO. To this solution is added 5.72 g (0.238 mol) of sodium hydride (washed with hexanes). The solution is heated to 60° C. for 1 hour. To this dark orange solution is added 50 mL of 4-chlorobenzotrifluoride (0.374 mol). The reaction mixture is heated to 115° C. for 6 hours. The reaction is allowed to cool to room temperature and then 1.0 L of water is added to quench the reaction. The reaction mixture is extracted with ethyl ether (2 times 500 mL), followed by two extractions using toluene (2 times 500 mL). The organic layers are combined and washed twice with brine. The aqueous layer is separated and the organic layer dried, filtered and rotoevaporated to yield 60.3 g of crude material. This crude material was purified by column chromatography (silica gel) using 5% methanol:methylene chloride as the eluent. Yield of pure fluoxetine free base is typically about 55%.

Example 4
Preparation of Fluoxetine Hydrochloride

To a 3.0 L round bottom flask is added 25.5 g (0.0824 mol) of fluoxetine free base. To this is added 850 mL of diethyl ether and the amine is dissolved. To this solution is added 150 mL of an ethereal hydrochloric acid solution (0.069 mol HCl/100 mL). The reaction is stirred for 30 minutes and then the ether is rotoevaporated to dryness. The solid was taken up in a minimum of ethyl acetate and hexane was added until crystals started forming. The white solid is placed in the refrigerator for 14 hours at about 5° C. The solution was filtered and dried to give 25.75 g of fluoxetine hydrochloride.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

References

The following references, to the extent that they provide exemplary procedural or other details supplementary to those set forth herein, are specifically incorporated herein by reference.

U.S. Pat. No. 4,194,009
U.S. Pat. No. 4,314,081
U.S. Pat. No. 4,902,710
U.S. Pat. No. 5,104,899
U.S. Pat. No. 5,166,437
U.S. Pat. No. 5,225,585
U.S. Pat. No. 5,760,243
U.S. Pat. No. 5,936,124
EP 380924
EP 457559
EP 529842
Span. Pat. No. , ES 2103681
Span. Pat. No. , ES 2101650
Finnish Pat. No. FI 81083
WO 94/00416
WO 0037425

WO 0144166
WO 9309769
WO 9906362
Ager and Laneman, Tet. *Asymmetry*, 30:3327–3355, 1997.
Arce, *Chem. Abstr.*, 129:260223, 1997.
Bartoli et al., *J. Chem. Soc.*, 1:537, 1994.
Chatterjee and Rudorf, In: *Phosphorus, Sulfur and Silicon and the Related Elements*, 1998, 133,251, 1988.
Chenevert, *Chem. Lett.*, 9:1603, 1991.
Clesse and Quinon, *Bull. Soc. Chim. Fr.*, 1940, 1969.
Corey and Reichard, *Tetrahedron Lett.*, 30:5207, 1989.
Foster et al., *Chem. Abstr.*, 113:31729, 1990.
Gao and Sharpless, *J. Org. Chem.*, 53:4081, 1988.
Hilborn et al., *Chem. Abstr.*, 131:170168, 1999.
Kairisalo et al., *Chem. Abstr.*, 114:42266, 1990.
Kumar et al., *Indian J. Chem.*, 31B:803–809, 1992.
Kumar et al., *Tetrahedron Lett.*, 32:1901, 1991.
Mitchell and Koenig, *Synth. Commun.*, 25:1231, 1995.
Pedregal, *Chem. Abstr.*, 128:114779, 1997.
Robertson et al. *J. Labeled Compound Radiopharm.*, 24:1397–1404, 1987.
Robertson et al., *J. Med. Chem.*, 31:1412, 1988.
Sakuraba and Achiwa, *Chem. Pharm. Bull.*, 43:748, 1995.
Sakuraba et al., *Syn. Lett.*, 689–690, 1991.
Schwartz et al., *Chem. Abstr.*, 119:8485, 1993.
Theriot, *Chem. Abstr.* 130:153652, 1999.
Theriot, *Chem. Abstr.*, 129:54356, 1998.
Weber and Marti, *Chem. Abstr.*, 133:58607, 2000.
Wirth et al., *Organic Proc. Res. Dev.*, 4:513, 2000.
Young and Barberich, *Chem. Abstr.*, 117:7635, 1992.
Young and Barberich, *Chem. Abstr.*, 119:203106, 1993.

What is claimed is:

1. A method comprising:
   a) synthesizing 1-phenyl-3-methylamino-2-propen-1-one by i) claisen condensation of acetophenone with ethyl formate leading to benzoylacetaldehyde sodium salt and ii) condensation of the benzoylacetaldehyde sodium salt with methylamine hydrochloride;
   b) converting 1-phenyl-3-methylamino-2-propen-1-one into 3-methylamino-1-phenyl-1-propanol using sodium borohydride and acetic acid; and
   c) converting 3-methylamino-1-phenyl-1-propanol to Fluoxetine hydrochloride.

2. The method of claim 1, wherein converting 1-phenyl-3-methylamino-2-propen-1-one into 3-methylamino-1-phenyl-1-propanol using a sodium borohydride and acetic acid comprises adding approximately 21 mmol of sodium borohydride to a solution comprising approximately 3.7 mmol of 3-methylamino-1-phenyl-2-propen-1-one in a glacial acetic acid solution producing a 3-methylamino-1-phenyl-1-propanol solution.

3. The method of claim 2, wherein the adding of sodium borohydride is performed at about 5 to 10° C.

4. The method of claim 2, further comprising adding approximately 240 mmol sodium hydroxide to the 3-methylamino-1-phenyl-1-propanol solution.

5. The method of claim 4, further comprising extracting the 3-methylamino-1-phenyl-1-propanol solution with ethyl acetate.

6. The method of claim 5, further comprising evaporating the ethyl acetate.

7. The method of claim 1, wherein converting 3methylamino-1-phenyl-1-propanol to Fluoxetine hydrochloride comprises:
   a) reacting 3-methylamino -1propanol with 4-chlorobenzotrifluoride in the presence of sodium borohydride in dimethylsulfoxide to give fluoxetine free base; and
   b) preparing fluoxetine hydrochloride by reacting the fluoxetine free base with hydrochloric acid in ether.

8. The method of claim 1, further comprising placing the fluoxetine hydrochloride in a pharmaceutical preparation.

9. The method of claim 8, wherein the pharmaceutical composition is administered to a subject.

10. A method of preparing 1-phenyl-3-methylamino-2-propen-1-one comprising:
    a) Claisen condensation of acetophenone with ethyl formate leading to benzoylacetaldehyde sodium salt; and
    b) condensation of the benzoylacetaldehyde sodium salt with a methylamine hydrochloride.

11. The method of claim 10, wherein the condensation of the crude benzoylacetaldehyde sodium salt with methylamine hydrochloride comprises adding approximately 29.4 mmol of benzoylacetaldehyde sodium salt to an solution containing approximately 148 mmol of methyl amine hydrochloride.

12. The method of claim 11, further comprising filtering, washing with water, and drying the 1-phenyl-3-methylamino-2-propen-1-one.

13. The method of claim 10, further comprising converting 1-phenyl-3-methylamino-2-propen-1-one into 3-methylamino-1-phenyl-1-propanol comprises adding approximately 21 mmol of sodium borohydride to a solution comprising approximately 3.7 mmol of 3-methylamino-1-phenyl-2-propen-1-one in a glacial acetic acid solution producing a 3-methylamino-1-phenyl-1-propanol solution.

* * * * *

UNITED STATES PATENT AND TRADEMARK OFFICE
CERTIFICATE OF CORRECTION

PATENT NO. : 6,846,957 B2
DATED : January 25, 2005
INVENTOR(S) : Zelenin

It is certified that error appears in the above-identified patent and that said Letters Patent is hereby corrected as shown below:

<u>Column 10,</u>
Line 16, delete "3-methylamino-1propanol" and insert -- 3-methylamino-1-phenyl-1propanol -- therefor.

Signed and Sealed this

Twelfth Day of July, 2005

JON W. DUDAS
*Director of the United States Patent and Trademark Office*